United States Patent [19] [11] 4,279,813

Schallner et al. [45] Jul. 21, 1981

[54] AQUEOUS PROCESS FOR THE PREPARATION OF AROMATIC PHOSPHORUS COMPOUNDS

[75] Inventors: Otto Schallner; Rainer Hamprecht, both of Cologne, Fed. Rep. of Germany

[73] Assignee: Bayer Aktiengesellschaft, Leverkusen, Fed. Rep. of Germany

[21] Appl. No.: 43,496

[22] Filed: May 29, 1979

[30] Foreign Application Priority Data

Jul. 6, 1978 [DE] Fed. Rep. of Germany ....... 2829710

[51] Int. Cl.$^3$ ....................... C09B 43/00

[52] U.S. Cl. ....................... 260/163; 260/198; 260/199; 260/200; 260/202; 260/204; 260/207.1; 260/208; 260/371; 260/969

[58] Field of Search ............... 260/152, 205, 206, 186, 260/187, 198, 199, 200, 201, 207, 207.1, 969, 163, 204, 371, 208

[56] References Cited

U.S. PATENT DOCUMENTS

| | | | |
|---|---|---|---|
| 3,493,639 | 2/1970 | Taus | 260/969 |
| 3,705,214 | 12/1972 | Martin | 260/969 |
| 4,104,270 | 8/1978 | Hall et al. | 260/205 X |

FOREIGN PATENT DOCUMENTS

| | | | |
|---|---|---|---|
| 2421070 | 11/1975 | Fed. Rep. of Germany | 260/969 |
| 2456495 | 8/1976 | Fed. Rep. of Germany | 260/207.1 |
| 2706854 | 8/1977 | Fed. Rep. of Germany | 260/207 |
| 2717091 | 11/1977 | Fed. Rep. of Germany | 260/969 |
| 1200273 | 7/1970 | United Kingdom | 260/969 |

*Primary Examiner*—Floyd D. Higel
*Attorney, Agent, or Firm*—Sprung, Felfe, Horn, Lynch & Kramer

[57] ABSTRACT

Phosphorus-containing compounds especially azo dyestuffs containing a grouping of the formula

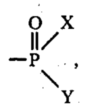

standing in ortho-position to the azo bridge are obtained in good yield if compounds of the formula

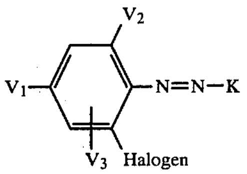

are reacted with compounds of the formula

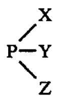

in aqueous medium at a pH of 6–9 in the presence of copper or copper containing compounds.

The process is less expensive than applying the conventional solvent method.

In the above formulae:

K = radical of a coupling component,
$V_1$-$V_3$ = H or non-ionic radical,
X and Y = —OR, —SR, —$NR_2$ or R,
R = optionally substituted hydrocarbon radical,
Z = —OR', —SR' or —$NR'_2$ and
R' = H or R.

11 Claims, No Drawings

AQUEOUS PROCESS FOR THE PREPARATION OF AROMATIC PHOSPHORUS COMPOUNDS

The invention relates to an improved process for the preparation of phosphorus-containing compounds of the formula

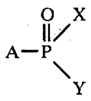
(I)

by reacting phosphorus compounds of the formula

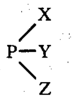
(II)

with activated aromatic halogen compounds of the formula

A—Hal (III)

wherein

- A represents an aromatic radical substituted by substituents with positive Hammet $\sigma$-para values,
- Hal represents halogen, preferably Cl, Br and I,
- X and Y independently of one another represent —OR, —SR, —$NR_2$ or R,
- R represents an optionally substituted hydrocarbon radical,
- Z represents —OR′, —SR′ or —$NR'_2$ and
- R′ represents H or R, in the presence of copper or copper compounds.

The new process is characterized in that this reaction is carried out in water.

It is surprising that this reaction which was hitherto only carried out in organic solvents proceeds smoothly and without complications in an aqueous medium, since it was known from DE-OS (German Published Specification) 2,706,854 and 2,717,091, that undesired side reactions take place in the presence of water.

Suitable aryl radicals A are radicals of the benzene, naphthalene, diphenyl and anthracene (in particular anthraquinone) series which are substituted in the manner indicated.

Suitable activating substituents in A are, above all, those with $\sigma$-para values of at least +0.3, preferably +0.5. Examples which may be mentioned are $NO_2$, CN, alkylsulphonyl, alkoxycarbonyl, alkylcarbonyl, arylazo and the like, which are preferably in the ortho-position and/or para-position relative to the halogen atom.

Suitable radicals R are: (a) $C_1$–$C_6$-alkyl radicals which are optionally substituted by $C_1$–$C_4$-alkoxy, phenyl or CN, (b) cyclohexyl radicals which are optionally substituted by methyl or Cl and (c) phenyl radicals which are optionally substituted by $C_1$–$C_4$-alkyl, $C_1$–$C_4$-alkoxy, $NO_2$ or Cl.

The products obtainable by the new process are valuable, known insecticides and starting substances for the preparation of polyurethanes (compare DE-OS (German Published Specification) 2,421,070).

The process according to the invention is particularly suitable for the preparation of azo dyestuffs which have at least one radical of the formula

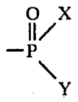

in the diazo component or coupling component in the orthoposition relative to the azo bridge.

The preferred representatives of such dyestuffs which are free from sulpho groups correspond to the formula

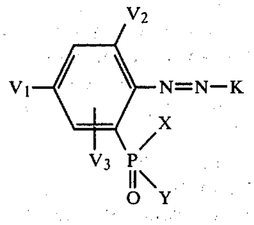
(VI)

wherein

- K denotes the radical of a coupling component,
- $V_1$–$V_3$ independently of one another denotes for hydrogen or a non-ionic substituent which is customary in dyestuff chemistry and
- X and Y have the abovementioned meaning.

Amongst these dyestuffs, those of the formula indicated wherein

- K represents a radical of the enol, pyrazolone or, above all, of the benzene or naphthalene series,
- $V_1$–$V_3$ represent H, Cl, Br, $C_1$–$C_4$-alkyl, $NO_2$, CN, phenylazo, $C_1$–$C_4$-alkoxy, $C_1$–$C_4$-alkoxycarbonyl, $C_1$–$C_4$-alkylcarbonyl, NHCO—$C_1$–$C_4$-alkyl or —$SO_2N(C_1$–$C_4$-alkyl$)_2$ and
- X and Y represent —OR″, wherein

- R″ denotes $C_1$–$C_4$-alkyl, benzyl, phenyl or phenylethyl, are in turn preferred.

Particularly preferred radicals K are those of the formula IX according to DE-AS (German Published Specification) 2,456,495, column 5.

Suitable enolic coupling components are open-chain coupling components (for example acetoacetic ester derivatives) or cyclic coupling components (for example barbituric acid derivatives)

Preferred dyestuffs containing sulpho groups correspond to the formula IV wherein

- K represents a hydroxy-, amino- or hydroxy/aminonaphthalenesulphonic acid radical and
- $V_1$–$V_3$ also represent —$SO_3H$, —COOH or —$PO_3H_2$.

The process products can furthermore also contain ammonium groups.

Starting materials which can be used for the preparation of these dyestuffs by the process according to the invention are corresponding ortho-halogenoazo dyestuffs, in particular those of the formula

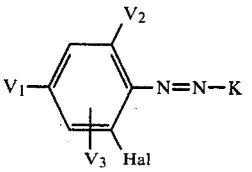

(V)

wherein the radicals indicated have the abovementioned meaning.

These compounds are generally known (compare, for example, U.S. Pat. Nos. 3,876,621 and 3,962,209).

The phosphorus compounds of the formula II are also known (compare the abovementioned German Offenlegungsschriften (German Published Specifications).

The reaction of II with III or V in water is generally effected at 10°-130° C., preferably 20°-100° C., and at pH values of 4-11, preferably 6-9. In general, equivalent amounts of II and III or V are employed, but a 1.5-3-fold excess of II is preferably used.

To accelerate the reaction, especially when water-insoluble compounds III or V are employed, it is advisable to add emulsifiers and/or phase transfer catalysts. The use of water-miscible, aprotic organic solvents in amounts of up to 5% (relative to the proportion of water) can also sometimes be of advantage.

Suitable solvents which can be used as activators for the reaction are, in particular, those of a basic nature, such as, for example, pyridine, triethylamine, 2,3,3-trimethylindolenine and other tertiary amines.

The copper catalysts are also in general employed in equivalent amounts, relative to the halogen to be replaced. However, catalytic amounts are also frequently adequate.

Suitable copper compounds are described in the abovementioned German Offenlegungsschriften (German Published Specifications). Cu-II salts, such as Cu-II sulphate and Cu-II acetate, are preferably employed.

The reaction times can vary within a broad range. In general, 1 to 12 hours are adequate for the reaction to be completed.

Compared with the known "solvent processes", the new process is distinguished, at about the same yields, by lower costs as a result of a lower expenditure on safety measures and omission of solvent recovery installations.

The process is illustrated in more detail with the aid of the following examples, in which "parts" denote parts by weight.

EXAMPLE 1 (METHOD A)

27 parts of sodium 1-(2'-bromo-4'-nitrophenylazo)-2-hydroxy-6-naphthylsulphonate are stirred with 130 ml of water, and 20 parts of copper sulphate 5-hydrate in 70 parts of water are added. The pH value is adjusted to 7-8 and the mixture is stirred for one hour. Thereafter, 35 parts of phosphorous acid diethyl ester are added dropwise at pH 8. The mixture is subsequently stirred at room temperature for 4 hours and acidified with hydrochloric acid. The precipitate is filtered off, washed and dried and gives 23 parts of diethyl 5-nitro-2-[2'-hydroxy-6'-sulphonaphthylazo]-phenylphosphonate almost free from starting compounds and by-products.

EXAMPLE 2 (METHOD B)

21 parts of 3-acetylamino-4-(2'-bromo-4',6'-dinitrophenylazo)-N,N-diethylaniline are stirred with 250 parts of water, 2 parts of an emulsifier based on polyether and 2 parts of 2,3,3-trimethylindolenine. 15 parts of copper sulphate 5-hydrate in 50 parts of water are added and the mixture is warmed to 80° C. 25 parts of diethyl phosphite or 31 parts of triethylphosphite are added to this mixture at a pH value of 8.

After 3-4 hours, the mixture is cooled to room temperature and brought to a pH value of 0.5-1 with hydrochloric acid. It is stirred for about 30 minutes and the dyestuff is filtered off, washed with water and dried. 19.7 parts of diethyl 3,5-dinitro-2-{2'-acetylamino-4'-N,N-diethylaminophenylazo}-phenylphosphonate, containing small amounts of starting material and by-products as impurities, are obtained.

If the procedure followed is as in the two preceding examples, but the starting materials listed in the table below are subjected to the conditions indicated, the reaction products mentioned in this table are obtained in about the same yields and qualities.

TABLE
| | Halogen compound | Phosphorus compound of the formula Z-PXY | Reaction temperature | Method | Reaction product 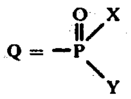 |
|---|---|---|---|---|---|
| (1) | 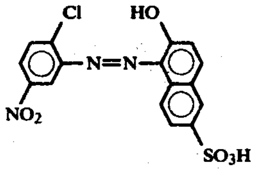 | Z = OH<br>Y = X = $OC_2H_5$ | 40° | A | 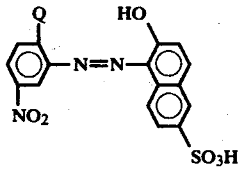 |
| (2) | 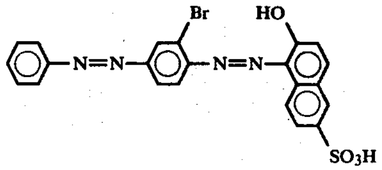 | Z = OH<br>Y = X = $OC_2H_5$ | 40° | A | 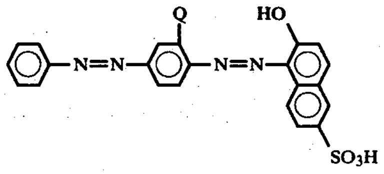 |
| (3) | 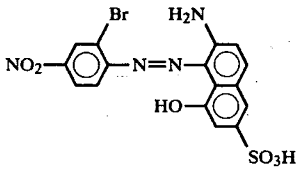 | Z = OH<br>Y = X = $OC_2H_5$ | 60° | A | 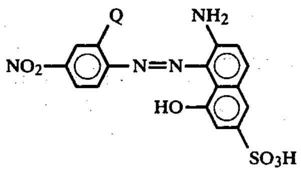 |
| (4) | 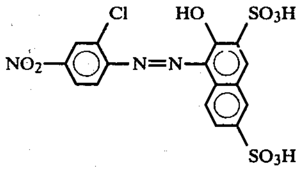 | Z = OH<br>X = Y = $OC_2H_5$ | 60° | A | 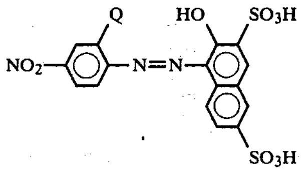 |
| (5) | 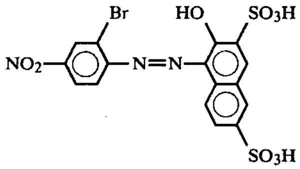 | Z = OH<br>X = Y = $OC_2H_5$ | 20° | A | 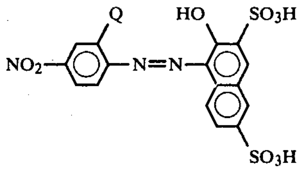 |

TABLE-continued
| | Halogen compound | Phosphorus compound of the formula Z-PXY | Reaction temperature | Method | Reaction product 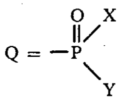 |
|---|---|---|---|---|---|
| (6) | 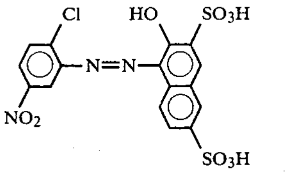 | Z = OH<br>X = Y = $OC_2H_5$ | 40° | A | 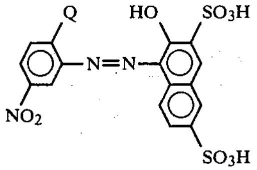 |
| (7) | 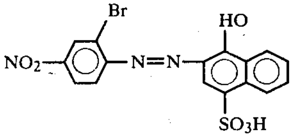 | Z = OH<br>X = Y = $OC_2H_5$ | 40° | A | 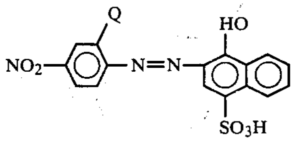 |
| (8) | 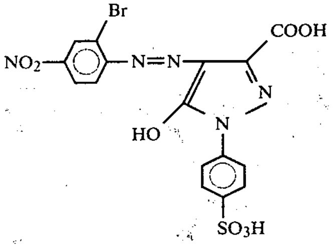 | Z = OH<br>X = Y = $OC_2H_5$ | 20° | A | 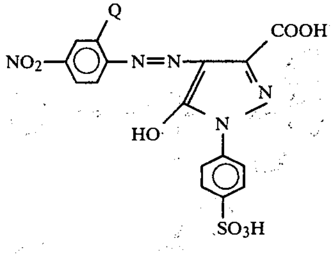 |
| (9) | 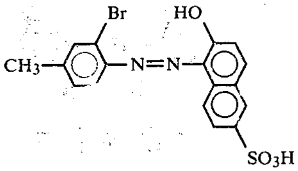 | Z = OH<br>X = Y = $OC_2H_5$ | 40° | A | 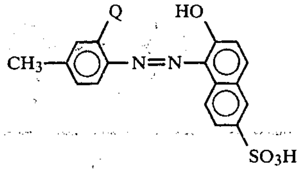 |
| (10) | 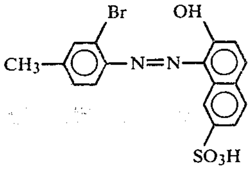 | Z = OH<br>X = Y = $OC_2H_5$ | 40° C. | A | 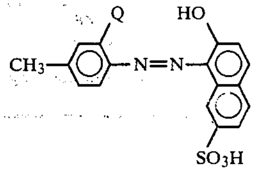 |

TABLE-continued
| | Halogen compound | Phosphorus compound of the formula Z-PXY | Reaction temperature | Method | Reaction product 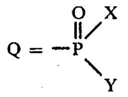 |
|---|---|---|---|---|---|
| (11) | 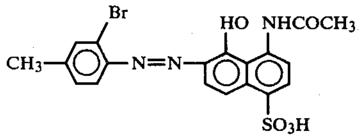 | Z = OH<br>X = Y = $OC_2H_5$ | 40° C. | A | 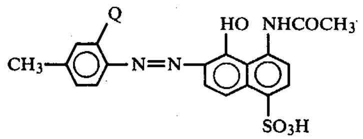 |
| (12) | 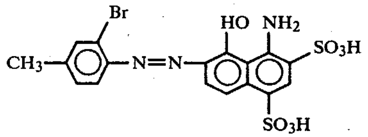 | Z = OH<br>X = Y = $OC_2H_5$ | 40° C. | A | 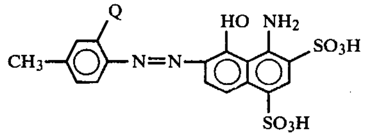 |
| (13) | 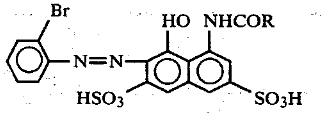<br>R = $CH_3$ oder $C_6H_5$ | Z = OH<br>X = Y = $OC_2H_5$ | 40° | A | 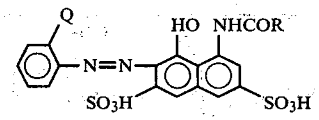 |
| (14) | 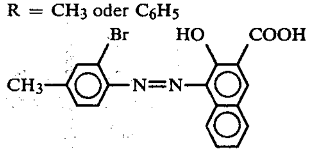 | Z = OH<br>X = Y = $OC_2H_5$ | 40° | A | 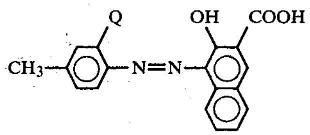 |
| (15) | 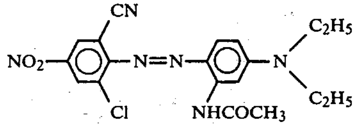 | Z = OH; X = Y = $OC_2H_5$ | 100° | B | 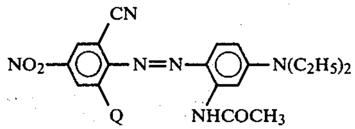 |
| (16) | 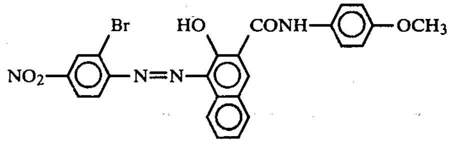 | Z = OH<br>X = Y = $OCH_5$ | 60° | B | 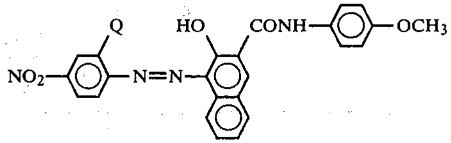 |
| (17) | 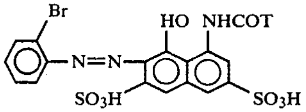<br>T = $CH_3$ oder $C_6H_5$ | X = Y = Z = O—i-$C_3H_7$ | 80° | A | 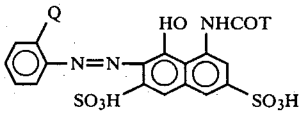 |

TABLE-continued
| | Halogen compound | Phosphorus compound of the formula Z-PXY | Reaction temperature | Method | Reaction product 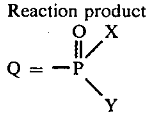 |
|---|---|---|---|---|---|
| (18) | 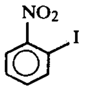 | Z = OH<br>X = Y = $OC_2H_5$ | 60° | B | 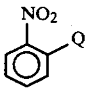 |
| (19) | 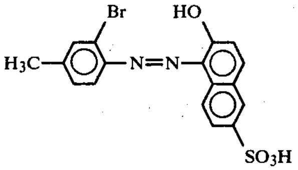 | Y = Z = $OC_2H_5$<br>X = $C_6H_5$ | 80° | A | 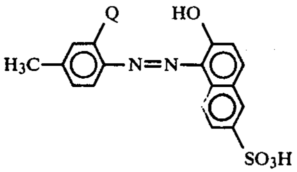 |
| (20) | 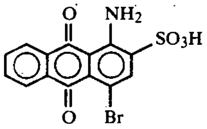 | Z = OH<br>X = Y = $OC_2H_5$ | 80° | A | 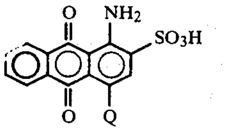 |
| (21) | 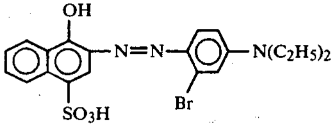 | Z = OH<br>X = Y = $OC_2H_5$ | 90° | A | 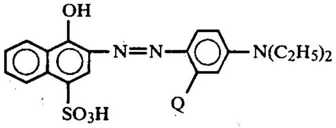 |

We claim:

1. In the preparation of a phosphorus-containing compound of the formula

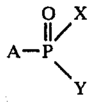

(I)

by reacting a phosphorus compound of the formula

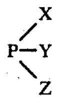

(II)

with an activated aromatic halogen compound of the formula

A—Hal (III)

wherein

A represents an aromatic radical substituted by substituents with positive Hammet σ-para values, Hal represents halogen, X and Y independently of one another represent —OR, —SR, —$NR_2$ or R, R represents $C_1$-$C_6$-alkyl, $C_1$-$C_6$-alkyl substituted by $C_1$-$C_4$-alkoxy, phenyl or CN, cyclohexyl, cyclohexyl substituted by methyl or Cl, phenyl, or phenyl substituted by $C_1$-$C_4$-alkyl, $C_1$-$C_4$-alkoxy, $NO_2$ or Cl, Z represents —OR', —SR, or —NR'$_2$ and R' represents H or R, in the presence of a Cu-II salt, the improvement comprising carrying out the reaction in an aqueous solution at a pH of 6-9.

2. Process according to claim 1, wherein an orthohalogenoazo dyestuff is employed as the halogen compound.

3. Process according to claim 1, wherein an azo dyestuff of the formula

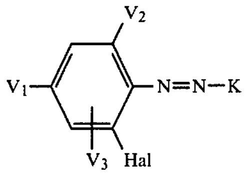

wherein

K denotes the radical of a coupling component and $V_1$-$V_3$ independently of one another represent hydrogen, Cl, Br, $C_1$-$C_4$-alkyl, $NO_2$, CN, phenylazo, $C_1$-$C_4$-alkylsulphonyl, $C_1$-$C_4$-alkoxycarbonyl, $C_1$-$C_4$-alkylcarbonyl, NHCO-$C_1$-$C_4$-alkyl, —$SO_2N(C_1$-$C_4$-alkyl$)_2$ or $C_1$-$C_4$-alkoxy, is employed as the halogen compound.

4. Process according to claim 3, wherein

K represents a hydroxy-, amino- or hydroxy-/aminonaphthalenesulphonic acid radical and $V_1$-$V_3$ also represents —$SO_3H$, —COOH or —$PO_3H_2$.

5. Process according to claim 3, wherein

K represents a radical of the phenol, pyrazolone, benzene or naphthalene series, X and Y represent —OR", and wherein R" denotes $C_1$-$C_4$-alkyl, benzyl, phenyl or phenylethyl is employed as the halogen compound.

6. Process according to claim 1, wherein the reaction is carried out in the presence of a tertiary amine.

7. Process according to claim 1, wherein the reaction is carried out in the presence of an emulsifier, a phase transfer catalyst or both.

8. Process according to claim 1, wherein a phosphorus acid ester is employed as the phosphorus compound.

9. Process according to claim 1 or 7, wherein a phosphorus acid ester of the formula

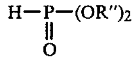

wherein

R" denotes $C_1$-$C_4$-alkyl, benzyl, phenyl or phenylethyl, is employed as the phosphorus compound.

10. Process according to claim 1, wherein the phosphorus compound which is employed is that of the formula indicated, and wherein Z represents —OR'.

11. The improvement according to claim 1, wherein Hal represents Cl, Br or I.

* * * * *